(12) United States Patent
Perschbacher et al.

(10) Patent No.: US 11,116,439 B2
(45) Date of Patent: Sep. 14, 2021

(54) SYSTEMS AND METHODS FOR DETECTING SLOW AND PERSISTENT CARDIAC RHYTHMS

(71) Applicant: Cardiac Pacemakers, Inc., St. Paul, MN (US)

(72) Inventors: David L. Perschbacher, Coon Rapids, MN (US); Sunipa Saha, Shoreview, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 493 days.

(21) Appl. No.: 16/180,586

(22) Filed: Nov. 5, 2018

(65) Prior Publication Data

US 2019/0167142 A1      Jun. 6, 2019

Related U.S. Application Data

(60) Provisional application No. 62/595,518, filed on Dec. 6, 2017.

(51) Int. Cl.
*A61B 5/364* (2021.01)
*A61B 5/024* (2006.01)
*A61B 5/361* (2021.01)
*A61B 5/363* (2021.01)

(52) U.S. Cl.
CPC .............. *A61B 5/364* (2021.01); *A61B 5/024* (2013.01); *A61B 5/361* (2021.01); *A61B 5/363* (2021.01)

(58) Field of Classification Search
CPC ......... A61B 5/364; A61B 5/361; A61B 5/363; A61B 5/324
See application file for complete search history.

(56) References Cited

U.S. PATENT DOCUMENTS

| 2007/0135848 A1* | 6/2007 | Kim ..................... A61N 1/3956 607/5 |
| 2009/0099616 A1* | 4/2009 | Li ........................... A61N 1/368 607/17 |

\* cited by examiner

*Primary Examiner* — Tammie K Marlen
(74) *Attorney, Agent, or Firm* — Schwegman Lundberg & Woessner, P.A.

(57) ABSTRACT

Systems and methods for detecting slow and persistent rhythms, such as indicative of ventricular response to atrial tachyarrhythmia (AT), are described herein. An arrhythmia detection system monitors patient ventricular heart rate, and identifies slow heart beats with corresponding heart rates falling below a rate threshold during a detection period. The system identifies one or more sustained slow beat (SSB) sequences each including two or more slow heart beats. The system determines a first prevalence indicator of the identified slow heart beats, and a second prevalence indicator of the identified SSB sequences during the detection period. An arrhythmia detector circuit detects a slow and persistent rhythm using the first and second prevalence indicators.

20 Claims, 5 Drawing Sheets

SYSTEMS AND METHODS FOR DETECTING SLOW AND PERSISTENT CARDIAC RHYTHMS

CLAIM OF PRIORITY

This application claims the benefit of priority under 35 U.S.C. § 119(e) of U.S. Provisional Patent Application Ser. No. 62/595,518, filed on Dec. 6, 2017, which is herein incorporated by reference in its entirety.

TECHNICAL FIELD

This document relates generally to medical devices, and more particularly, to systems, devices and methods for detecting and managing cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs can detect cardiac arrhythmias, such as atrial tachyarrhythmia (AT). One type of AT is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself. Persistent AF may last for over a week and typically requires medication or other treatment to revert to normal sinus rhythm. AF is permanent if a normal heart rhythm cannot be restored with treatment.

Another type of AT is atrial flutter (AFL). AFL usually accompanies with some degree of atrioventricular (AV) node conduction block, and can be associated with a fast and usually regular heart rate. Typical or Type I AFL may involve a single reentrant circuit in the right atrium around the tricuspid valve annulus, and has an atrial rate of 240 to 340 beats per minute (bpm). The reentrant circuit most often travels in a counter-clockwise direction. Atypical or Type II AFL follows a different circuit, which may involve the right or the left atrium, and usually has a faster atrial rate of around 340-440 bpm. AFL may be associated with a variety of cardiac disorders, such as coronary artery disease (CAD) or hypertensive heart disease. AFL may often degenerate into AR Prolonged fast AFL may lead to decompensation with loss of normal heart function. This may manifest as effort intolerance, nocturnal breathlessness, or swelling of the legs or abdomen.

Timely detection of AT, such as AF or AFL, may be clinically important for assessing cardiac function. Some atrial tachyarrhythmia may be characterized by slow and stable ventricular rates. Such arrhythmic episodes may be mistakenly recognized by an IMD as a sinus rhythm, and stay undetected or under-detected in some patients. This may adversely impact patient outcome.

OVERVIEW

Atrial tachyarrhythmia such as AF or AFL are characterized by fast atrial rate. In some patients, direct sensing of atrial activation rate with an electrode positioned in the atrium is not available or not feasible, such as patients not indicated for atrial lead implantation. A medical device, such as a single-chamber IMD with no dedicated atrial sensing/pacing lead, may detect the AT based on ventricular heart rate, without direct sensing of atrial activity. However, confounding factors such as noise, motion artifacts, or cardiac rhythms other than the AT may be mistakenly detected as AT events. For example, during AFL, impulses from the atria are conducted to the ventricles through the atria-ventricular node (AV node). Due primarily to its longer refractory period, the AV node may exert a protective effect on heart rate at the ventricle by blocking atrial impulses in excess of approximately 180 beats per minute (bpm). If an AFL rate is 300 bpm, a two-to-one (2:1) heart block may develop such that only half of the atrial impulses can be conducted to the ventricle, resulting in a ventricular rate of 150 bpm. As the heart rate is a measure of the ventricular rather than atrial activity, a medical device that detects AT based on ventricular heart rate and not on atrial activity may be confounded by physiological sinus rhythm at an elevated rate such as during tolerable physical activities (e.g., sinus tachycardia).

In some patients, atrial tachyarrhythmia accompanied by slow ventricular rate may sustain for an extended period (e.g., over 10 hours or 24 hours) For example, conducted atrial activations from AFL may result in slow and stable ventricular rhythm. AF in the presence of AV block may result in slow and stable ventricular rates due to a junctional rhythm such as either an escape rhythm during complete AV block or an accelerated junctional pacemaker. An IMD, or an external computerized arrhythmia detection system, may falsely detect the AF or AFL episodes with slow and persistent ventricular rate as a sinus rhythm or other non-tachyarrhythmia events. When such arrhythmic events stay undetected or under-detected, adverse patient outcome may result.

Inappropriate detection of an AT episode may decrease detection specificity, and result in lack or treatment or untimely treatment, or unnecessary or inappropriate medical or device therapies. False alerts to clinicians of the inappropriately detected arrhythmia, or presenting to clinicians a large volume of inappropriately detected arrhythmic events for review or adjudication, may adversely affect the device efficacy and unwarrantedly increase the healthcare cost associated with patient management. Consequently, this may diminish the clinical utility of the heart rate-based AT detection. For at least these reasons, the present inventors have recognized, among other things, substantial challenges and a demand for a more efficient system and methods for detecting AT.

This document discusses, among other things, systems, devices, and methods for detecting slow and persistent rhythms, which may be indicative of ongoing atrial tachyarrhythmia. An arrhythmia detection system includes a heart rate analyzer circuit to monitor patient heart rate corresponding to a plurality of heart beats. The heart rate analyzer circuit may identify, during a detection period, slow heart beats with corresponding heart rates falling below a rate threshold. The heart rate analyzer circuit may additionally identify one or more sustained slow beat (SSB) sequences each including two or more slow heart beats. The heart rate analyzer may determine a first prevalence indicator of the identified slow heart beats, and a second prevalence indicator of the identified SSB sequences. An arrhythmia detector circuit may detect a slow and persistent rhythm based on at least the first and second prevalence indicators.

Example 1 is a system for detecting cardiac arrhythmias. The system comprises a heart rate analyzer circuit and an arrhythmia detector circuit. The heart rate analyzer circuit may be configured to monitor a ventricular heart rate corresponding to a plurality of heart beats, to identify, from the plurality of heart beats during a detection period, slow heart beats with corresponding heart rates falling below a rate threshold, to identify, during the detection period, one or more sustained slow beat (SSB) sequences each including two or more of the slow heart beats. The arrhythmia detector circuit may be configured to detect a slow and persistent rhythm based on the identified slow heart beats and the identified one or more SSB sequences.

In Example 2, the subject matter of Example 1 optionally includes the heart rate analyzer circuit that may be configured to determine a first prevalence indicator of the identified slow heart beats, and a second prevalence indicator of the one or more SSB sequences. The arrhythmia detector circuit that may be configured to detect the slow and persistent rhythm when (1) the first determined prevalence indicator exceeds a first prevalence threshold, and (2) the second determined prevalence indicator exceeds a second prevalence threshold. In an example, the second prevalence threshold is different than the first prevalence threshold.

In Example 3, the subject matter of Example 2 optionally includes the heart rate analyzer circuit that may be configured to determine the first prevalence indicator based on an accumulated duration of the identified slow heart beats, and to determine the second prevalence indicator based on a duration of a longest SSB sequence among the identified one or more SSB sequences.

In Example 4, the subject matter of any one or more of Examples 2-3 optionally includes the heart rate analyzer circuit that may be configured to determine the second prevalence indicator based on an accumulated duration of a subset of the identified one or more SSB sequences each exceeding an SSB duration threshold.

In Example 5, the subject matter of any one or more of Examples 1-4 optionally includes the SSB sequences each of which may be represented by a consecutive sequence of two or more of the identified slow heart beats.

In Example 6, the subject matter of any one or more of Examples 1-4 optionally includes the SSB sequences each of which may be represented by a beat sequence that includes, for any ten consecutive heart beats within the beat sequence, at least six slow heart beats.

In Example 7, the subject matter of any one or more of Examples 1-6 optionally includes the arrhythmia detector circuit that may be configured to detect the slow and persistent rhythm including an atrial arrhythmia with slow and persistent ventricular response.

In Example 8, the subject matter of any one or more of Examples 2-7 optionally includes the heart rate analyzer circuit that may be configured to: determine a representative ventricular heart rate for each of a plurality of heart rate analysis windows, the plurality of heart rate analysis windows each including two or more of the plurality of heart beats; identify, from the plurality of heart rate analysis windows during the detection period, slow rate windows with corresponding representative ventricular heart rates falling below the rate threshold; identify, during the detection period, one or more sustained slow window (SSW) sequences each including two or more of the identified slow rate windows; and determine the first prevalence indicator indicating a number of the identified slow rate windows, and a second prevalence indicator of the identified one or more SSW sequences.

In Example 9, the subject matter of Example 8 optionally includes the representative ventricular heart rate that may include a central tendency of the heart rates in a heart rate analysis window.

In Example 10, the subject matter of any one or more of Examples 8-9 optionally includes the one or more SSW sequences each of which may be represented by a consecutive sequence of slow rate windows. The heart rate analyzer circuit may be configured to identify a longest SSW sequence among the identified SSW sequences, and to determine the second prevalence indicator indicating a number of slow rate windows in the identified longest SSW sequence.

In Example 11, the subject matter of Example 10 optionally includes the arrhythmia detector circuit that may be configured to detect an atrial arrhythmia with slow and persistent ventricular response, during a detection period of 24 hours, when (1) the number of the identified slow rate windows exceeds a first threshold of 400; and (2) the number of slow rate windows in the identified longest consecutive sequence exceeds a second threshold of 100.

In Example 12, the subject matter of any one or more of Examples 8-9 optionally includes the one or more SSW sequences each of which may be represented by a consecutive sequence of slow rate windows. The heart rate analyzer circuit may be configured to identify a subset of the SSW sequences each exceeding an SSW duration threshold, and to determine the second prevalence indicator based on an accumulated number of slow rate windows of the identified subset of SSW sequences.

In Example 13, the subject matter of any one or more of Examples 8-9 optionally includes the one or more SSW sequences each of which may be represented by a sequence of heart rate analysis window that includes, for any ten consecutive heat rate analysis windows within the sequence, at least six slow rate windows. The heart rate analyzer circuit may be configured to identify a longest SSW sequence among the identified SSW sequences, and to determine the second prevalence indicator indicating a number of heart rate analysis windows included in the identified longest SSW sequence.

In Example 14, the subject matter of any one or more of Examples 2-13 optionally includes an activity detection circuit that may be configured to detect patient physical activity, and a sensing circuit that may be configured to sense heart beats during physical activity of different intensity levels. The heart rate analyzer circuit may be configured to determine the first and second prevalence indicators using the ventricular heart rates sensed during the physical activities of different intensity levels.

In Example 15, the subject matter of any one or more of Examples 1-14 optionally includes a therapy circuit that may be configured to generate a therapy for delivery to a target tissue in response to the detection of the slow and persistent rhythm.

Example 16 is a method for detecting cardiac arrhythmias using a medical system. The method comprises steps of: monitoring ventricular heart rates corresponding to a plurality of heart beats using a heart rate analyzer circuit; identifying, from the plurality of heart beats during a detection period, slow heart beats with corresponding heart rates falling below a rate threshold using the heart rate analyzer circuit; identifying, during the detection period, one or more sustained slow beat (SSB) sequences each including two or more of the slow heart beats using the heart rate analyzer circuit; and detecting a slow and persistent rhythm based on the identified slow heart beats and the identified one or more SSB sequences.

In Example 17, the subject matter of Example 16 optionally includes determining a first prevalence indicator of the identified slow heart beats, and a second prevalence indicator of the one or more SSB sequences using heart rate analyzer circuit, and detecting the slow and persistent rhythm including determining that the first determined prevalence indicator exceeds a first prevalence threshold and the second determined prevalence indicator exceeds a second prevalence threshold.

In Example 18, the subject matter of Example 17 optionally includes the first prevalence indicator including an accumulated duration of the identified slow heart beats. The second prevalence indicator may include a duration of a longest SSB sequence among the identified one or more SSB sequences.

In Example 19, the subject matter of Example 17 optionally includes the second prevalence indicator including an accumulated duration of a subset of the identified one or more SSB sequences each exceeding an SSB duration threshold.

In Example 20, the subject matter of Example 16 optionally includes the SSB sequences each of which may be represented by a consecutive sequence of two or more of the identified slow heart beats.

In Example 21, the subject matter of Example 16 optionally includes the SSB sequences each of which may be represented by a beat sequence that includes, for any ten consecutive heart beats within the beat sequence, at least six slow heart beats.

In Example 22, the subject matter of Example 76 optionally includes steps of: determining representative ventricular heart rates for each of a plurality of heart rate analysis windows, the plurality of heart rate analysis windows each including two or more of the plurality of heart beats; identifying, from the plurality of heart rate analysis windows during the detection period, slow rate windows with corresponding representative ventricular heart rates falling below the rate threshold; identifying, during the detection period, one or more sustained slow window (SSW) sequences each including two or more of the identified slow rate windows; and determining the first prevalence indicator indicating a number of the identified slow rate windows, and a second prevalence indicator of the identified one or more SSW sequences.

In Example 23, the subject matter of Example 16 optionally includes delivering a therapy to a target tissue in response to the detection of the slow and persistent rhythm.

The systems, devices, and methods discussed in this document may improve the medical technology of automated cardiac rhythm management (CRM) and prevention of worsening of cardiac function. The automated detection of slow and persistent rhythms, such as indicative of an ongoing AT episode, may enhance the performance and functionality of an implantable medical device. In certain examples, the slow and persistent rhythm detection may improve sensitivity and specificity of existing AF or AFL detection, with little to no additional cost, while reducing costs associated with false AT detections, or manual inspection required by such false determinations. In other examples, existing system performance can be maintained (e.g., high arrhythmia detection sensitivity and specificity, etc.) using lower cost or less obtrusive systems, apparatus, and methods. For example, because the system or device does not require direct sensing of atrial activity, the system complexity and implementation cost may be reduced. It may particularly be beneficial for patient not indicated for atrial lead implantation either for atrial activity sensing or for atrial pacing. The arrhythmia detection discussed in this document may also allow for more efficient use of device memory, such as by storing indicators of prevalence of slow heart beats and prevalence of sustained slow beat sequences, among other heart beat statistics, which are clinically relevant to AT detection. With improved AT detection, fewer alarms are provided, battery life can be extended, fewer unnecessary drugs and procedures may be scheduled, prescribed, or provided, and an overall system cost and. power savings may be realized in contrast to existing medical devices and systems.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting slow and persistent rhythms. In an embodiment, an arrhythmia detection system monitors patient ventricular heart rate, and identifies slow heart heats with corresponding heart rates falling below a rate threshold during a detection period. The system identifies one or more sustained slow beat sequences each including two or more slow heart beats.

An arrhythmia detector circuit may detect a slow and persistent rhythm, such as an AT episode, based on a first prevalence indicator of the identified slow heart beats, and a second prevalence indicator of the identified SSB sequences.

Figure 1:
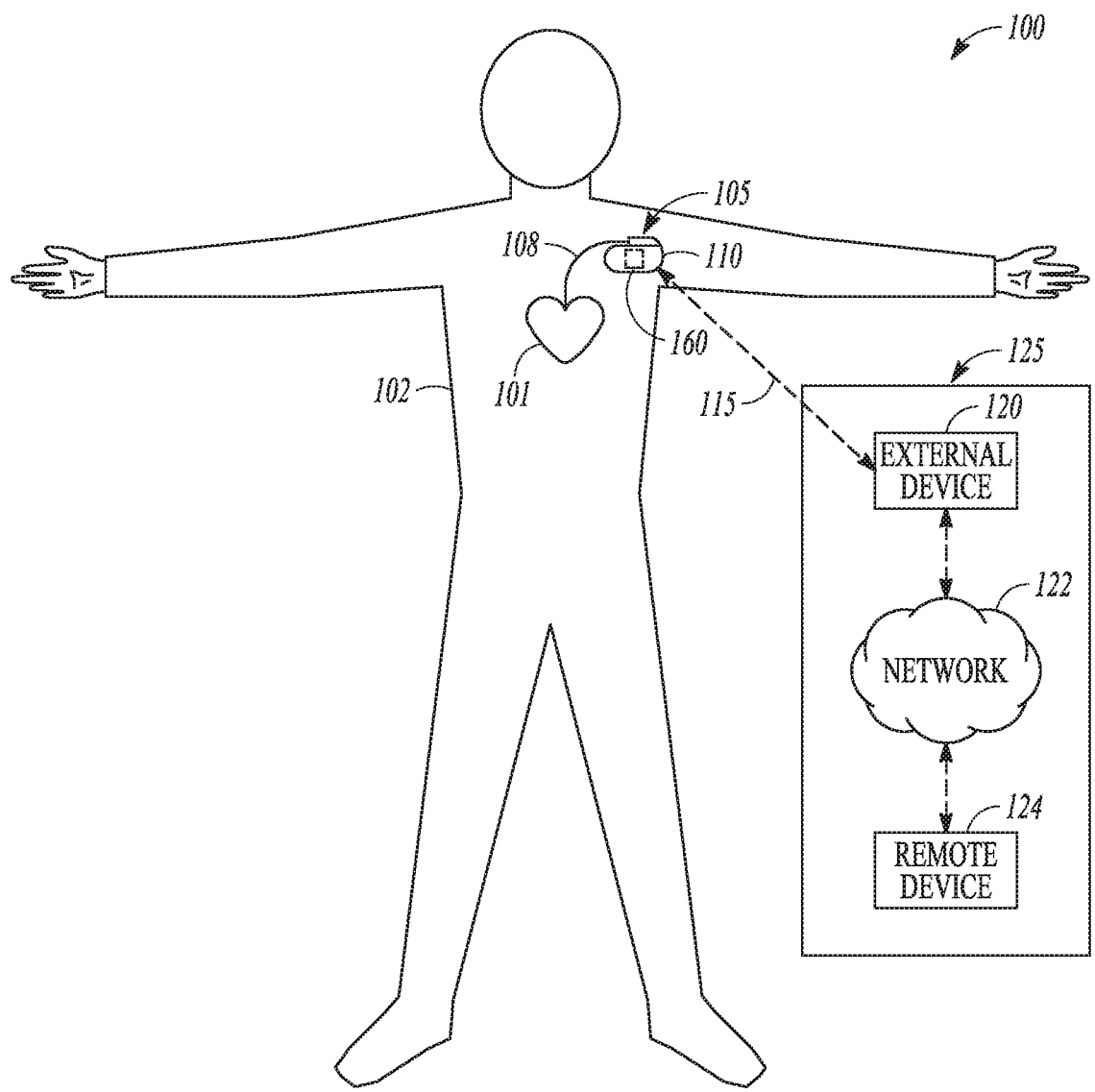
FIG. 1 illustrates an example of a Cardiac Rhythm Management (CRM) system and portions of an environment in which the CRM system may operate.

FIG. 1 illustrates generally an example of a Cardiac Rhythm Management (CRM) system 100 and portions of an environment in which the system 100 may operate. The CRM system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may alternatively or additionally include subcutaneously implanted devices, wearable devices, or other external monitoring or therapeutic medical devices or equipment.

The AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be configured to be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient ventricular heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiological response to activity, posture, respiration tidal volume, respiratory sounds, body weight, or body temperature.

In an example, the AMD 110 may include a cardiac arrhythmia detection circuit 160 configured to detect a slow and persistent cardiac rhythm from the patient 102. The slow and persistent cardiac rhythm may be represented by ongoing atrial tachyarrhythmia, such as an AFL or AF episode. The sensed physiological signal contains information about patient ventricular heart rate or pulse rate. The cardiac arrhythmia detection circuit 160 may generate ventricular heart rate statistics from the sensed physiological signal. The ventricular heart rate statistics may indicate sustained excessive heart rate throughout a specific period of duration. The cardiac arrhythmia detection circuit 160 may detect the slow and persistent cardiac rhythm in response to the ventricular heart rate statistics satisfy specific conditions. The AMD 110 may output the detected slow and sustained rhythm to a user such as the patient or a clinician, or to a process including, for example, an instance of a computer program executable in a microprocessor. In an example, the process may include an automated generation of recommendations for anti-arrhythmic therapy, or a recommendation for further diagnostic test or treatment.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

Although the discussion herein with respect to the AMD 110 focuses on implantable system, this is meant only by way of example and not limitation. It is within the contemplation of the inventors and within the scope of this document, that the systems, devices, and methods discussed herein may also be implemented in, and executed by, a subcutaneous medical device such as a subcutaneous monitor or diagnostic device, wearable devices (e.g., watch-like devices, patch-based devices, or other accessories), or other ambulatory medical devices.

The external system 125 may be communicated with the AMD 110 via a communication link 115. The external system 125 may include a dedicated hardware/software system such as a programmer, a remote server-based patient management system, or alternatively a system defined predominantly by software running on a standard personal computer. The external system 125 may be used to control the operation of the AMD 110. The external system 125 may additionally receive via the communication link 115 information acquired by AMD 110, such as one or more physiological signals.

By way of example and not limitation, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, a capacitive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), analyzing the physiological data to detect cardiac arrhythmias, or optionally delivering or adjusting a therapy to the patient 102.

One or more of the external device 120 or the remote device 124 may include a display for displaying the physiological or functional signals, or alerts, alarms, emergency calls, or other forms of warnings to signal the detection of arrhythmias. In some examples, the external system 125 may include an external data processor configured to analyze the physiological or functional signals received by the AMD 110, and to confirm or reject the detection of arrhythmias. Computationally intensive algorithms, such as machine-learning algorithms, may be implemented in the external data processor to process the data retrospectively to detect cardia arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
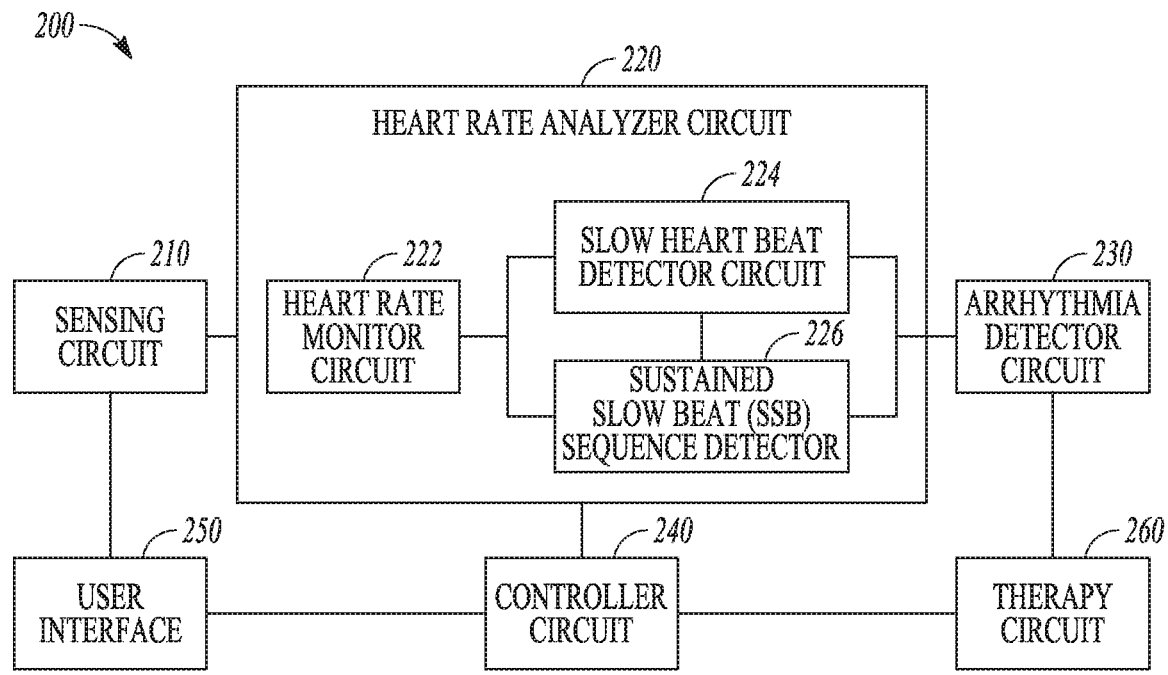
FIG. 2 illustrates generally an example of an arrhythmia detection system configured to detect slow and persistent rhythms from a patient.

FIG. 2 illustrates generally an example of an arrhythmia detection system 200 configured to detect slow and persistent rhythms from a patient. The slow and persistent rhythm may be indicative of ongoing atrial tachyarrhythmia, such as an AF or AFL episode. Portions of the arrhythmia detection 200 may be included in the arrhythmia detection circuit 160 of the AMD 110. The arrhythmia detection system 200 may include one or more of a sensor circuit 210, a heart rate analyzer circuit 220, an arrhythmia detector circuit 230, a controller circuit 240, and a user interface unit 250. The arrhythmia detection system 200 may be configured as a cardiac monitor or diagnostic device for monitoring patient health status, or as a therapeutic device that additionally includes an optional therapy circuit 260.

The sensor circuit 210 may include a sense amplifier circuit to sense a physiological signal from a patient via one or more implantable, wearable, or otherwise ambulatory sensors or electrodes associated with the patient. The sensed physiological signal may contain information about pulsatile cardiac activity, such as heart rate or pulse rate. Examples of the physiological signals may include surface electrocardiography (ECG) such as sensed from electrodes on the body surface, subcutaneous ECG such as sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more other sub-circuits to digitize, filter, or perform other signal conditioning operations on the received physiological signal.

In some examples, the physiological signals may be stored in a storage device such as an electronic medical record system. The sensor circuit 210 may retrieve a physiological signal from the storage device in response to a command signal that is provided by a system user, or automatically generated in response to occurrence of a specific event.

The heart rate analyzer circuit 220 may be coupled to the sensor circuit 210 to monitor a ventricular heart rate, and to detect slow heart beats. The heart rate analyzer circuit 220 may include a heart rate monitor circuit 222, a slow heart beat detector 224, and a sustained slow beat (SSB) sequence detector 226. The heart rate monitor circuit 222 may sense heart beats from the sensed physiological signal, and detect heart rate. In an example, the sensor circuit 210 may sense a cardiac electrical signal such as an ECG, a subcutaneous ECG, or an intracardiac EGM, and the heart rate monitor circuit 222 may detect from the cardiac electrical signal electrophysiological events indicative of cardiac depolarization or repolarization. Examples of the sensed electrophysiological events may include P wave, Q wave, R wave, QRS complex, or T wave in a surface or subcutaneous ECG or an intracardiac EGM. The sensor circuit 210 may additionally or alternatively include one or more sensors configured to sense cardiac mechanical activity indicative of heart contractions, and the heart rate monitor circuit 222 may sense from the sensed cardiac mechanical activity mechano-physiological events indicative of one or more of atrial contraction, ventricular contraction, end of filling, end of emptying, or other specified phase during a cardiac contraction cycle. Examples of the sensors for sensing cardiac mechanical activity may include an accelerometer or a microphone configured to sense a heart sound signal or an endocardial acceleration signal from the heart, an impedance sensor configured to sense cyclic changes in cardiac impedance as a result of cardiac contractions, or a blood pressure sensor or a blood flow sensor for sensing pulsatile arterial pressure or flow as a result of cyclic cardiac contractions and opening/closure of heart valves, among other sensors. Examples of the mechano-physiological events may include: S1, S2, S3, or S4 heart sound from the sensed heart sound signal, peak or trough impedance from the cardiac impedance signal, or peak or trough blood pressure from the blood pressure signal, among others.

The heart rate analyzer circuit 220 may detect the ventricular heart rates using the detected electrophysiological or mechano-physiological events. In an example, cardiac cycles (CLs) may be measured a time interval (such as in a unit of second or millisecond) between two adjacent R waves (R-R interval) or P waves (P-P interval), or between adjacent impedance peaks or adjacent impedance troughs from the cardiac impedance signal, or an interval between two adjacent blood pressure peaks (i. e., systolic pressure) or adjacent blood pressure troughs (i. e., diastolic pressure) from the blood pressure signal, among others. The CL may be converted to heart rate (in beats per minute, or bpm) using the formula HR=60 seconds/CL.

In various examples, the heart rate analyzer circuit 220 may detect the ventricular heart rates under a specified patient condition, such as when the patient is physically active, or during a specified time of day. The system 200 may include a physical activity detection circuit coupled to an activity sensor to detect patient physical activity. The physical activity sensor may be an implantable, wearable, holdable, or otherwise ambulatory sensor for sensing an intensity of physical activity of the subject. The physical activity sensor may include a single-axis or a multi-axis accelerometer configured to sense an acceleration signal of at least a portion of the subject's body. The strength of the acceleration signal can be indicative of the physical activity level. In another example, the activity sensor can include a respiratory sensor configured to measure respiratory parameters correlative or indicative of respiratory exchange, i. e., oxygen uptake and carbon dioxide output. In another example, patient physical activity information can be derived from thoracic impedance information. The sensing circuit 210 may sense heart beats during physical activity of different intensity levels.

The slow heart beat detector 224 may identify, from the plurality of heart beats during a detection period, slow heart beats with corresponding heart rates falling below a rate threshold $HR_{TH}$. The rate threshold $HR_{TH}$ may be programmable. In an example, the rate threshold $HR_{TH}$ is approximately 50-70 beats per minute (bpm) to detect slow and persistent rhythms. The detection period may be specified by a user, and programmed into the heart beat detector 224. In an example, the detection period is approximately 10 hours. In another example, the detection period is approximately 24 hours.

The slow heart beat detector 224 may further determine a first prevalence indicator of the identified slow heart beats. The prevalence indicator may be represented by accumulated duration ($T_{SB}$, in milliseconds, or msec) of the cardiac cycles of the identified slow heart beats during the detection period. Alternatively, the prevalence indicator may be represented by a count ($N_{SB}$) of the identified slow heart beats during the detection period.

In some examples, the heart rate monitor circuit 222 may determine a representative ventricular heart rate (rHR) using the sensed heart beats within a heart rate analysis window. The heart rate analysis window has a specific length, represented by specified number of heart beats or a time duration. The length of the heart rate analysis window may be programmable, such as adjustable by a user via the user interface unit 250. In an example, the heart rate analysis window is approximately 2-5 minutes. Examples of the rHR may include a mean, a median, a mode, or other central tendency of a plurality of heart rate measurements within the heart rate analysis window. For example, a mode of the heart rate measurements may indicate most frequently occurring heart rate value in the plurality of heart rate measurements. Alternatively, the rHR may be computed as a specific percentile (e.g., X-th percentile) of the heart rate measurements, a heart rate greater than X % of the heart rate measurements in a frequency distribution of heart rate measurements. In an example, a heart rate histogram may be generated from the heart rate measurements within the heart rate analysis window, and the X % is approximately between 25-75%. Representative heart rate is a more robust estimate of the heart rate during atrial tachyarrhythmia. Statistical measurement (e.g., the central tendency or a specific percentile of heart rate distribution) may have improved immunity to noise and interference, and reduced chances of heart rate oversensing or undersensing. It may also reduce the effect of intermittent conduction of the atrial impulses to the ventricle on heart rate detection.

The slow heart beat detector 224 may identify, from the plurality of heart rate analysis windows during the detection period, slow rate windows with the corresponding representative heart rates falling below the rate threshold $HR_{TH}$. Similar to the first prevalence indicator of the slow heart rates as discussed above, the slow heart beat detector 224 may alternatively determine a first prevalence indicator of the identified slow rate windows based on accumulated duration ($T_{SW}$) of the identified slow rate windows, or a count ($N_{SW}$) of the identified slow rate windows during the detection period. Examples of determining representative heart rates are discussed below, such as with reference to FIG. 4.

The sustained slow beat (SSB) sequence detector circuit 226 may be configured to identify one or more sustained slow beat (SSB) sequences during the detection period. Each of the one or more SSB sequences may include two or more of the identified slow heart beats. In an example, an SSB sequence may be represented by a consecutive sequence of two or more slow heart beats. The minimum number of consecutive slow heart beats required for an SSB sequence may be programmable and adjusted by a user such as via the user interface 250. In another example, an SSB sequence may be represented by a beat sequence that includes at least a specified fraction (e.g., a percentage) of slow beats out of a given subset of beats taken from the sequence. In an example, an SSB sequence is identified as having at least X slow heart beats within any Y consecutive heart beats within the beat sequence. This criterion for identifying an SSB sequence is hereinafter referred to as an "X/Y" criterion. The values of X and Y in the X/Y criterion may be programmable and adjusted by a user such as via the user interface 250. By ways of non-limiting example, X/Y criterion may include 6/10 or 5/8 criterion.

The SSB sequence detector 226 may further determine a second prevalence indicator of the identified SSB sequences. In an example, the second prevalence indicator may be determined based on the longest SSB sequence among the identified SSB sequences during the detection period. The second prevalence indicator may include a duration ($T_{SSB}$) of a longest SSB sequence, or a count ($N_{SSB}$) of slow beats included in the longest SSB sequence. Alternatively, the second prevalence indicator may be determined based on a subset of the identified SSB sequences each of which exceeds an SSB duration threshold, One example of the SSB duration threshold is approximately 5 hours. Another example of the SSB duration threshold is approximately 400 slow beats in an SSB sequence. The second prevalence indicator may be computed based on accumulated duration (in msec) of the subset of SSB sequences, or based on an accumulated count of heart beats included in the subset of SSB sequences.

Like the slow heart beat detector 224 that may identify slow rate windows based on the representative heart rates (rHRs), the SSB sequence detector 226 may alternatively identify, during the detection period, one or more sustained slow window (SSW) sequences each including two or more of the identified slow rate windows with respective rHRs falling below the $HR_{TH}$. In an example, an SSW sequence may be represented by a consecutive sequence of two or more slow rate windows. The minimum number of consecutive slaw rate windows required for an SSW sequence may be programmable and adjusted by a user. Alternatively, the SSW sequences may be identified using the "X/Y" criterion as discussed above for identifying the SSB sequences, such that an SSW sequence includes at least X slow rate windows within any Y consecutive heart beat windows. By ways of non-limiting example, X/Y criterion may include 6/10 or 5/8 criterion. Examples of identifying SSW sequences based on consecutive sequence of slow rate windows, or based on X/Y criterion, are discussed below, such as with reference to FIG. 5.

The SSB sequence detector 226 may determine the second prevalence indicator of the identified SSW sequences based on the longest SSW sequence, such as a duration ($T_{SSW}$), or a count ($N_{SSW}$) of heart rate analysis windows included in the longest SSW sequence. Alternatively, the second prevalence indicator may be determined based on a subset of the identified SSW sequences each of which exceeds an SSW duration threshold. The second prevalence indicator may be computed based on accumulated duration (in msec) of the subset of SSW sequences, or based on an accumulated count of heart rate analysis windows in the subset of SSW sequences.

In various examples, the sensing circuit 210 may be configured to sense heart beats when the patient undergoes physical activities with different intensity levels. The heart rate analyzer circuit 220 may monitor heart rates, identify slow heart beats (or slow rate windows) and SSB sequences (or SSW sequences), and determine the first and second prevalence indicators using the heart rates associated with corresponding physical activity intensity levels.

The arrhythmia detector circuit 230 may be configured to detect a slow and persistent rhythm based on at least the first and second prevalence indicators. The slow and persistent rhythm may be indicative of an atrial tachyarrhythmia, such as atrial fibrillation (AF), atrial flutter (AFL), atrial tachycardia, or paroxysmal supraventricular tachycardia (PSVT), among others. Examples of detecting slow and persistent rhythm are discussed below, such as with reference to FIG. 3.

As illustrated in FIG. 2, the heart rate analyzer circuit 220 or the arrhythmia detector circuit 230 may respectively include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, the heart rate analyzer circuit 220 or the arrhythmia detector circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the sensor circuit 210. Alternatively, the microprocessor circuit may be a general-purpose processor that may receive and execute a set of instructions of performing the functions, methods, or techniques described herein.

The controller circuit 240 controls the operations of the sensor circuit 210, the heart rate analyzer circuit 220, the arrhythmia detector circuit 230, the user interface unit 250, and the data and instruction flow between these components. For example, the controller circuit 240 may control the slow heart beat detection and prevalence determination, the SSB or SSW sequence identification and prevalence determination, and arrhythmia detection. The user interface unit 250 may include an input device and an output device. In an example, at least a portion of the user interface unit 250 may be implemented in the external system 130. The input device may receive a user's programming input, such as parameters for detecting the slow heart beat and SSB or SSW sequences. The input device may include a keyboard, on-screen keyboard, mouse, trackball, touchpad, touch-screen, or other pointing or navigating devices. The input device may enable a system user to program the parameters used for sensing the physiological signals, detecting the arrhythmias, and generating alerts, among others.

The output device may generate a human-perceptible presentation of the detected slow and persistent rhythm. The output device may include a display for displaying the sensed physiological signal, intermediate measurements or computations such as slow heart beats counts and SSB sequence duration, among others. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected arrhythmic events.

The optional therapy circuit 260 may be configured to deliver a therapy to the patient in response to the detection of the slow and persistent rhythm. Examples of the therapy may include electrostimulation therapy delivered to the heart, a nerve tissue, other target tissues, a cardioversion therapy, a defibrillation therapy, or drug therapy. In some examples, the therapy circuit 260 may modify an existing therapy, such as adjust a stimulation parameter or drug dosage.

Figure 3:
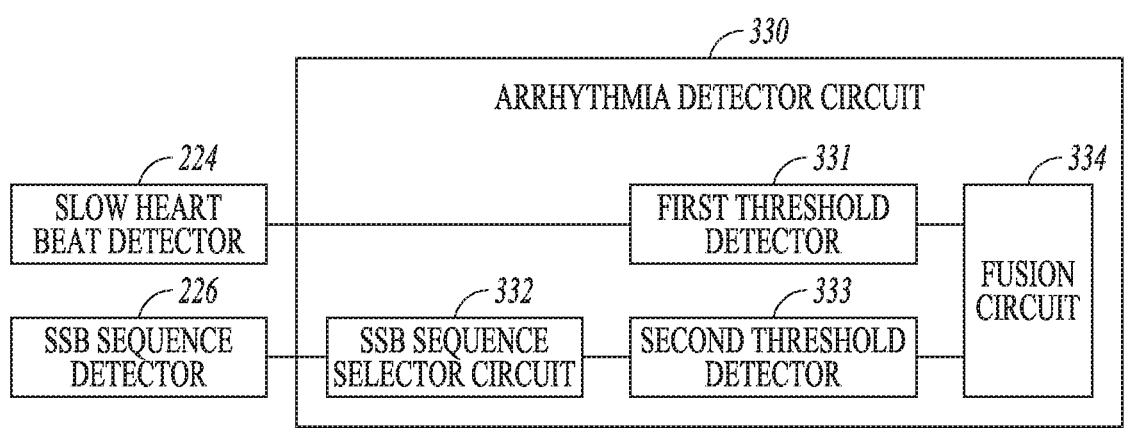
FIG. 3 illustrates generally an example of an arrhythmia detector circuit for detecting a slow and persistent rhythm indicative of an ongoing atrial tachyarrhythmia episode.

FIG. 3 illustrates generally an example of an arrhythmia detector circuit 330 for detecting a slow and persistent rhythm, such as one indicative of an ongoing atrial tachyarrhythmia such as AFL or AF. The arrhythmia detector circuit 330 is an embodiment of the arrhythmia detector 230 of the system 200. As illustrated in FIG. 3, the arrhythmia detector circuit 330 may include a first threshold detector 331 for detecting whether the first prevalence indicator (e.g., $T_{SB}$ or $N_{SB}$, or $T_{SW}$ or $N_{SW}$), generated by the slow heart beat detector 224, exceeds a first prevalence threshold. The arrhythmia detector circuit 330 includes an SSB sequence selector circuit 332 for selecting between a longest SSB sequence and a subset of SSB sequences that satisfy a duration criterion, or between a longest SSW sequence and a subset of SSW sequences that satisfy a duration criterion, as detected by the SSB sequence detector 226. For the selected sequence (or a set of sequences), the corresponding second prevalence indicators (e.g., $T_{SSB}$ or $N_{SSB}$, or $T_{SSW}$ or $N_{SSW}$) may be compared to a second prevalence threshold. A second threshold detector 333 may detect whether the second prevalence indicator exceeds the second prevalence threshold. A fusion circuit 334 may detect a slow and persistent rhythm by combining the decisions made at the first threshold detector 331 and the second threshold detector 333. In an example, a slow and persistent rhythm is detected when (1) the first prevalence indicator exceeds a first prevalence threshold, and (2) the second prevalence indicator exceeds a second prevalence threshold. In an example, the arrhythmia detector circuit 230 may detect an atrial tachyarrhythmia with slow and persistent ventricular response during a detection period of 24 hours. Such an atrial tachyarrhythmia is deemed detected if (1) $N_{SW}$ is greater than a first prevalence threshold of approximately 400 slow rate windows, and (2) $N_{SSW}$ of the identified longest consecutive SSB sequence is greater than a second prevalence threshold of approximately 100 slow rate windows.

In some examples, the detection of slow and persistent rhythm may be further based on ventricular heart rate stability representing a degree of variability or regularity of ventricular response. Examples of the heart rate stability may include difference, variance, standard deviation, or other higher-order statistics that characterize the variability of the cycle length or heart rate. In an example, the heart rate stability may be computed using a histogram of the plurality of heart rates or representative hear rates (rHRs) computed from the heart rate analysis windows. In another example, the heart rate stability may be derived from Lorenz plot (LP) of the rHRs. The LP is a scatterplot of the present heart rate or cycle length (CL) as a function of the preceding one or more CLs or heart rates. The LP-based stability may include geometric indices generated from the LP of the CLs or HRs, such as maximal length of the LP shape, maximal width of the LP shape, a density or spreadness measure of the LP scatterplots, among others.

Figure 4:
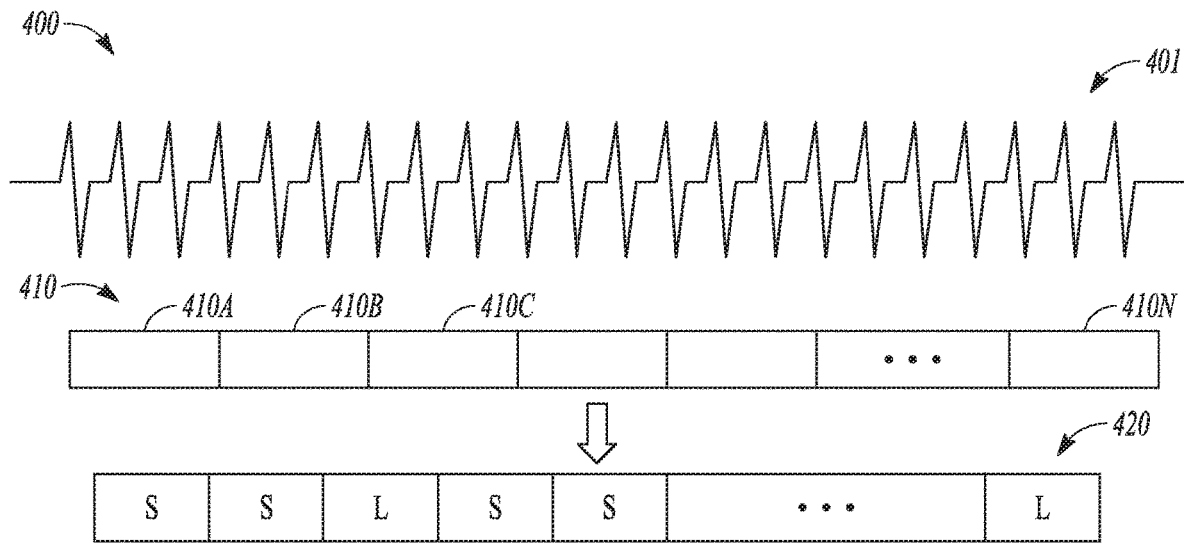
FIG. 4 is a graph illustrating an example of determining representative heart rates within respective heart rate analysis windows.

FIG. 4 illustrates a graph 400 of an example of determining representative heart rates within respective heart rate analysis windows. A physiological signal 401 may contain information about pulsatile cardiac electrical or mechanical activities. Heart rates may be detected via, for example, the heart rate monitor circuit 222. A window set 410, which includes a plurality of heart rate analysis windows 410A, 410B, . . . , 410N, may be applied to the physiological signal 401. Representative ventricular heart rates (rHRs) may be computed within each heart rate analysis window. In the illustrated example, the window set 410 includes N consecutive, non-overlapping heart rate analysis windows. In other examples, at least some heart rate analysis windows may overlap. Each heart rate analysis window may have a specific size, represented by a specific number of heart beats or a specific time period. In an example, the heart rate analysis window has a size of approximately 2-5 minutes. The rHRs may each be computed as central tendency (e.g., a mode) of the heart rate measurements within their respective heart rate analysis window, such as by using the slow heart beat detector 224. The rHRs may be compared to a heart rate threshold $HR_{TH}$. A heart rate analysis window may be designated as a slow rate window (denoted as "S" in FIG. 4) if $rHR<HR_{TH}$, or designated as a fast heart rate (or long CL, denoted as "L" in FIG. 4) if $rHR \geq HR_{TH}$. For example, window 410A is a slow rate window, and 410C is a fast rate window. As such, the window set 410 may correspond to the rHR train 420. The slow heart beat detector 224 may generate the first prevalence indicator, such as $N_{SW}$, by counting the slow rate windows out of the rHR train 420. The SSB sequence detector 226 may also identify one or more SSW sequences from the rHR train 420.

Figure 5:
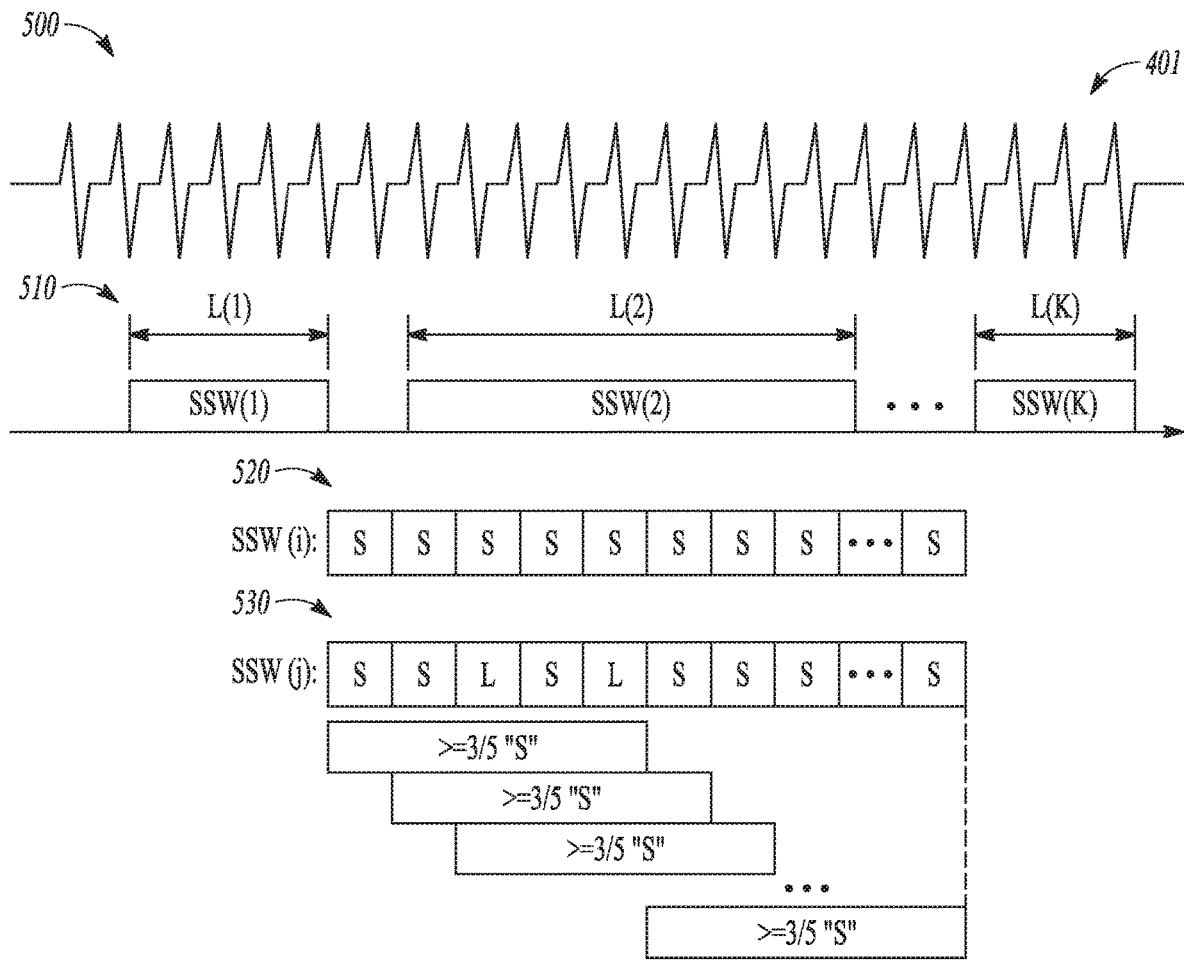
FIG. 5 is a graph illustrating examples of identifying sustained slow beat sequences or sustained slow window sequences.

FIG. 5 illustrates a graph 500 of examples of identifying sustained slow beat (SSB) sequences or sustained slow window (SSW) sequences. Heart rates may be detected from the physiological signal 401 such as using the heart rate monitor circuit 222. In the illustrated example, a set of SSB or SSW sequences are identified, such as by using the SSB sequence detector 226. As previously discussed, an SSB sequence is a sequence of individual heart beats, and an SSW sequence is a sequence of heart rate analysis windows. By way of example and not limitation, FIG. 5 illustrates a set of SSW sequences 510 including SSW(1), SSW(2), SSW (K). FIG. 5 illustrates two different representations of an SSW sequence. In one example, the sequence SSW(i) 520 consists of consecutive slow rate windows ("S"). In another example, sequenced SSW(j) 530 consists of both slow rate windows ("S") and fast rate windows ("L"), where for any five consecutive heart rate windows within the beat sequence, at least three are slow rate windows. That is, the sequence SSW(j) satisfies "X/Y" criterion, where X/Y is 3/5 in this example to identify an SSW sequence. It is to be understood that other X/Y criterion, such as 6/10, or 5/8, may be used to identify an SSW sequence.

In an example, the SSB sequence detector 226 identifies all SSW sequences {SSW(1), SSW(2), SSW(K)} using the criterion of consecutive slow rate windows. In another example, the SSB sequence detector 226 identifies all SSW sequences {SSW(1), SSW(2), SSW(K)} using the "X/Y" slow windows criterion with a uniform X value and uniform Y value. In some examples, the SSB sequence detector 226 may identify the SSW sequences using either consecutive slow rate windows criterion or the "X/Y" slow windows criterion.

The identified SSW sequences each have respective length or duration, denoted by L(1), L(2), . . . , L(K). Each L(i) may be represented by the number of heart beats included in the corresponding sequence SSW(i). In one example, the SSB sequence detector 226 may determine a prevalence of the SSW sequence as the length of the longest SSW sequence, that is, $N_{SSW}=\max(L(i))$ for i=1, 2, K. In another example, the SSB sequence detector 226 may determine the prevalence of the SSW sequence as an aggregated length of a subset of the SSW sequences that exceeds a specified sequence length duration ($L_{TH}$). For example, if each of the SSW sequences {SSW(1), SSW(2), SSW(K)} is longer than $L_{TH}$, then the prevalence of the SSW sequence can be determined as $N_{SSB}=L(1)+L(2)+ \ldots L(K)$. The prevalence $N_{SSB}$ may be used to detect slow and persistent rhythm, such as using the arrhythmia detector circuit 230 or 330.

Figure 6:
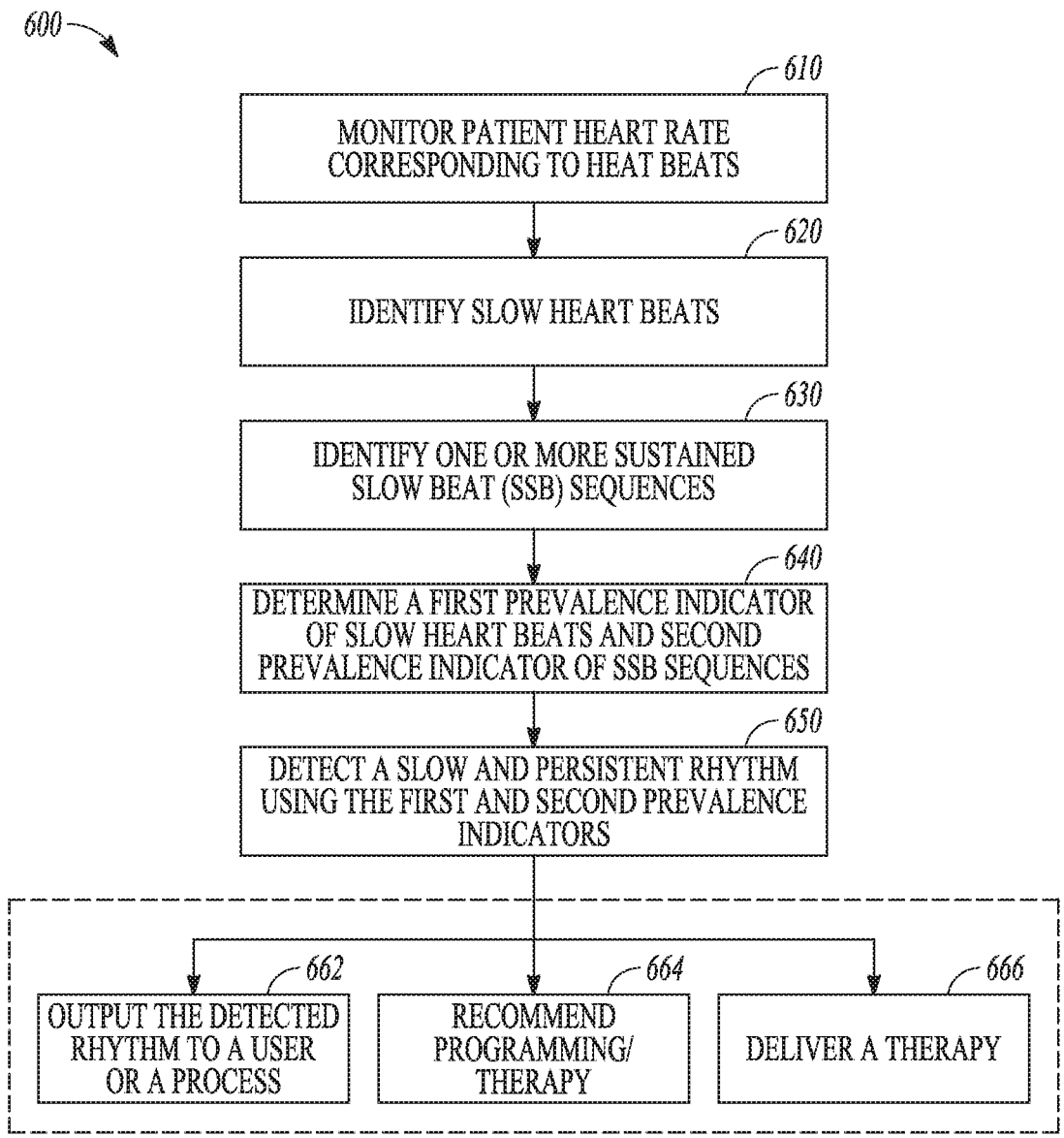
FIG. 6 illustrates generally an example of a method for detecting a slow and persistent rhythm from a patient.

FIG. 6 illustrates generally an example of a method 600 for detecting a slow and persistent rhythm from a patient. The slow and persistent rhythm may represent an ongoing atrial tachyarrhythmia, such as an atrial fibrillation (AF), atrial flutter (AFL), atrial tachycardia, paroxysmal supraventricular tachycardia (PSVT), or other atrial tachyarrhythmia. The method 600 may be implemented and executed in an ambulatory medical device such as an implantable or wearable device, or in a remote patient management system. In an example, the method 600 may be implemented in and executed by the cardiac arrhythmia detection circuit 160 in the AMD 110, the external system 130, or the arrhythmia detection system 200.

The method 600 commences at step 610, where patient ventricular heart rate may be monitored. Ventricular heart rates may be determined from a plurality of heart beats detected from a physiological signal sensed from a patient. Examples of the physiological signals may include a cardiac electrical signal, or signals indicative of cardiac mechanical activity. In some examples, ventricular heart rates may be monitored under a specified patient condition, such as when the patient undergoes physical activities, or during a specified time of day. The sensed physiological signal may be pre-processed, including amplification, digitization, filtering, or other signal conditioning operations. In some examples, the heart rates may be detected from a physiological signal stored in a storage device, such as an electronic medical record system.

At 620, slow heart beats may be detected during a detection period. The slow heart beats are those with corresponding heart rates falling below a rate threshold $HR_{TH}$. In an example, $HR_{TH}$ is approximately 50-70 beats per minute (bpm). The detection period may be programmable, and specified by a user. In an example, the detection period is approximately 10-24 hours.

In various example, a representative ventricular heart rate (rHR) within a heart rate analysis window may be used to identify slow rate windows. The rHR may be determined as a mean, a median, a mode, or other central tendency of a plurality of heart rate measurements within the heart rate analysis window. In an example, the heart rate analysis window has a size of approximately 2-5 minutes. Alternatively, the rHR may be computed as a specific percentile of the heart rate measurements. In an example, the percentile is between $25^{th}$ and $75^{th}$ percentile. At 620, slow rate windows, such as those having corresponding rHRs falling below the heart rate threshold $HR_{TH}$, may be identified front the plurality of heart rate analysis windows during the detection period.

At 630, one or more sustained slow beat (SSB) sequences may be identified. An SSB sequence may be represented by a consecutive sequence of two or more slow heart beats. The minimum number of consecutive slow heart beats required for an SSB sequence may be programmable. Alternatively, an SSB sequence may be represented by a beat sequence that includes at least a specified fraction of slow heats out of a given subset of beats taken from the sequence. In an example, an SSB sequence satisfies an X/Y criterion, where there are at least X slow heart beats within any Y consecutive heart beats within the beat sequence.

In some examples, at 630, one or more sustained slow window (SSW) sequences may be identified during the detection period. Each SSW sequence includes two or more slow rate windows with respective rHRs falling below the $HR_{TH}$. An SSW sequence may be represented by a consecutive sequence of two or more slow rate windows. Alternatively, an SSW sequence may be identified using the X/Y criterion, such that illustrated in FIG. 5 where, by way of example and not limitation, a 3/5 criterion is used to identify a SSW sequence.

At 640, a first indicator of prevalence of the identified slow heart beats (or the identified slow rate windows) during the detection period may be determined. The first prevalence indicator may be represented by accumulated duration ($T_{SB}$) of the identified slow heart beats, or accumulated duration ($T_{SW}$) of the identified slow rate windows, during the detection period. Alternatively, the first prevalence indicator may be represented by a count ($N_{SB}$) of the identified slow heart beats, or a count ($N_{SW}$) of the identified slow rate windows, during the detection period.

Also at 640, a second indicator of prevalence of the identified SSB sequences (or the identified SSW sequences) during the detection period may be determined, In an example, a longest SSB sequence may be identified from all the identified SSB sequences during the detection period. The second prevalence indicator may be represented by a duration ($T_{SSB}$) of the longest SSB sequence, or a count ($N_{SSB}$) of slow beats included in the longest SSB sequence. Alternatively, the second prevalence indicator may be determined based on a subset of the identified SSB sequences each of which exceeds an SSB duration threshold. In an example, the SSB duration threshold is approximately 5 hours. In another example, the SSB duration threshold is approximately 400 slow heart beats in an SSB sequence. The second prevalence indicator may be represented by an accumulated duration of the subset of SSB sequences, or an accumulated count of beats included in the subset of SSB sequences.

In some examples, the second prevalence indicator may be determined using the identified SSW sequences. In an example, the second prevalence indicator may be represented by a duration ($T_{SSW}$) of the longest SSW sequence, or a count ($N_{SSW}$) of heart rate analysis windows included in the longest SSW sequence. Alternatively, the second prevalence indicator may be determined based on a subset of the identified SSW sequences each of which exceeds an SSW duration threshold. In an example, the second prevalence indicator may be represented by an accumulated duration of the subset of SSW sequences, or an accumulated count of slow beats included in the subset of SSW sequences.

At 650, a slow and persistent rhythm may be detected using at least the first and second prevalence indicators, such as using the arrhythmia detector circuit 330. In an example, the detection of the slow and persistent rhythm includes comparing the first prevalence indicator (e.g., $T_{SB}$ or $N_{SB}$, or $T_{SW}$ or $N_{SW}$) to a first prevalence threshold, and comparing the second prevalence indicators (e.g., $T_{SSB}$ or $N_{SSB}$, or $T_{SSW}$ or $N_{SSW}$) a second prevalence threshold. A slow and persistent rhythm is detected when the first prevalence indicator exceeds a first prevalence threshold, and the second prevalence indicator exceeds a second prevalence threshold. In an example, detection of an atrial tachyarrhythmia with slow and persistent ventricular response may be performed during a detection period of 24 hours, By way of example and not limitation, a slow rate window is defined as a 2-minute heart beat window with a representative heart rate (rHR) less than 70 bpm. A detection is declared if $N_{SW}$ is greater than a first prevalence threshold of approximately 400 slow rate windows, and $N_{SSW}$ of the identified longest consecutive SSB sequence is greater than a second prevalence threshold of approximately 100 slow rate windows.

The detected slow and persistent rhythm may be provided to one or more of the processes 662, 664, or 666. At 662, the slow and persistent rhythm may be output to a user or a process, such as via an output device of the user interface 250. In an example, the detected rhythm may be displayed on a display, including the sensed physiological signal, information about the identified slow heart beats or slow rate windows, SSB sequences or SSW sequences or their respective prevalence indicators, among others. Additionally or alternatively, a hard copy of the detection information may be generated. In various examples, alerts, alarms, emergency calls, or other forms of warnings to signal may be generated to warn the system user about the detected rhythm.

At 664, a recommendation may be generated and provided to a user. The recommendation may include one or more of further diagnostic tests to be performed, antiarrhythmic therapy to treat the detected arrhythmia or to alleviate the arrhythmic complications. The recommendation may include adjustment of one or more arrhythmia detection parameters, such as the heart rate threshold $HR_{TH}$ for detecting slow heart beats, or threshold values for the first and second prevalence indicators. The method 600 may include the optional step 666 of delivering a therapy to the patient in response to the detection of the slow and persistent rhythm, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia.

Figure 7:
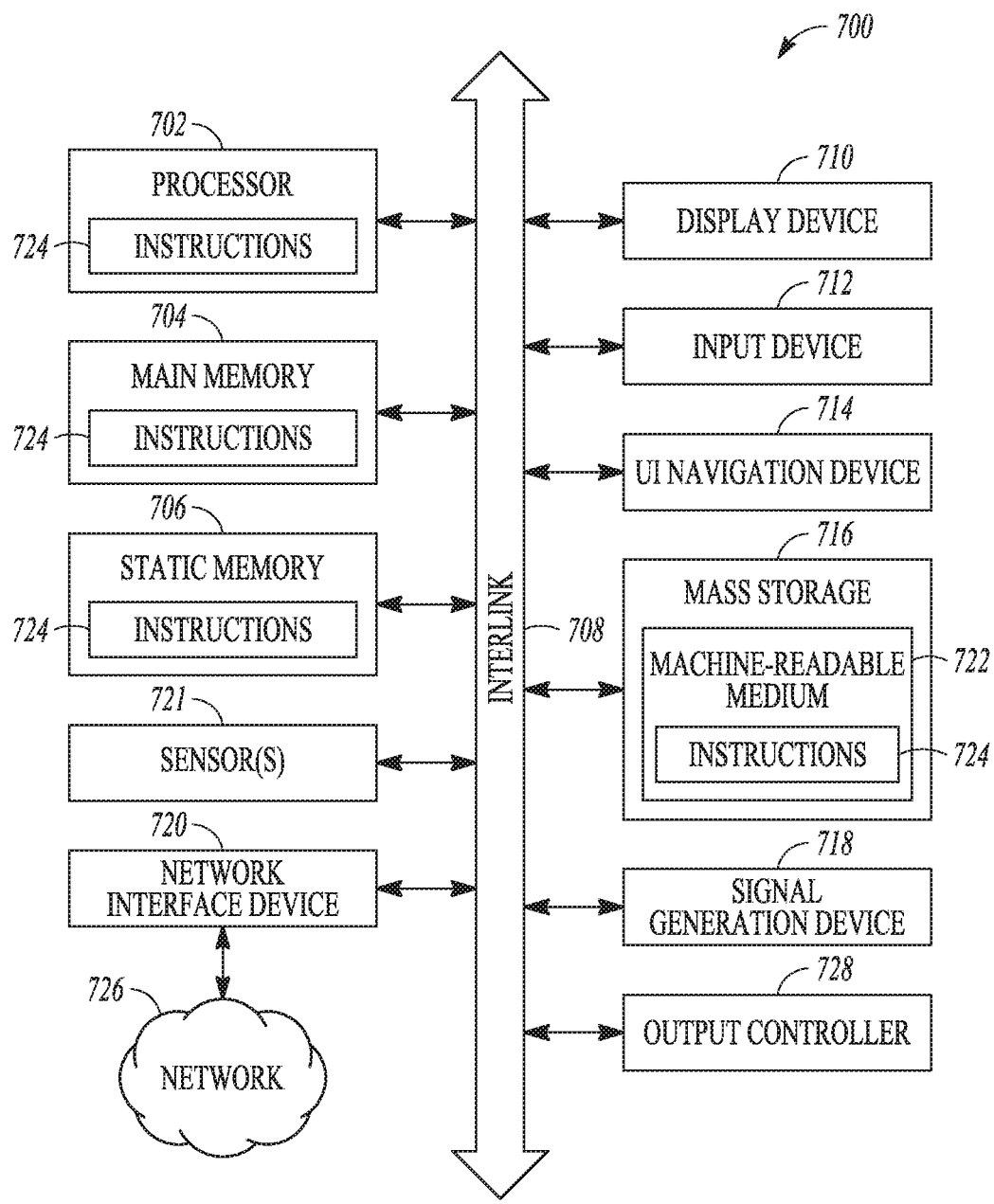
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine-readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802. 11 family of standards known as WiFi®, IEEE 802. 16 family of standards known as WiMax®), IEEE 802. 15. 4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for detecting cardiac arrhythmias, comprising:
    a heart rate analyzer circuit configured to:
        monitor a ventricular heart rate corresponding to a plurality of heart beats;
        identify, from the plurality of heart beats during a detection period, slow heart beats with corresponding heart rates falling below a rate threshold; and
        identify, during the detection period, one or more sustained slow beat (SSB) sequences each including two or more of the slow heart beats; and
    an arrhythmia detector circuit configured to detect a slow and persistent rhythm based on the identified slow heart beats and the identified one or more SSB sequences.

2. The system of claim 1, wherein the heart rate analyzer circuit is configured to determine a first prevalence indicator of the identified slow heart beats, and a second prevalence indicator of the one or more SSB sequences, and the arrhythmia detector circuit is configured to detect the slow and persistent rhythm when (1) the first determined prevalence indicator exceeds a first prevalence threshold, and (2) the second determined prevalence indicator exceeds a second prevalence threshold.

3. The system of claim 2, wherein the heart rate analyzer circuit is configured to determine the first prevalence indicator based on an accumulated duration of the identified slow heart beats, and to determine the second prevalence indicator based on a duration of a longest SSB sequence among the identified one or more SSB sequences.

4. The system of claim 2, wherein the heart rate analyzer circuit is configured to determine the second prevalence indicator based on an accumulated duration of a subset of the identified one or more SSB sequences each exceeding an SSB duration threshold.

5. The system of claim 2, wherein the heart rate analyzer circuit is configured to:
    determine a representative ventricular heart rate for each of a plurality of heart rate analysis windows, the plurality of heart rate analysis windows each including two or more of the plurality of heart beats;
    identify, from the plurality of heart rate analysis windows during the detection period, slow rate windows with corresponding representative ventricular heart rates falling below the rate threshold;
    identify, during the detection period, one or more sustained slow window (SSW) sequences each including two or more of the identified slow rate windows; and
    determine the first prevalence indicator indicating a number of the identified slow rate windows, and a second prevalence indicator of the identified one or more SSW sequences.

6. The system of claim 5, wherein the one or more SSW sequences are each represented by a consecutive sequence of slow rate windows, and
    wherein the heart rate analyzer circuit is configured to identify a longest SSW sequence among the identified SSW sequences, and to determine the second prevalence indicator indicating a number of slow rate windows in the identified longest SSW sequence.

7. The system of claim 6, wherein the arrhythmia detector circuit is configured to detect an atrial arrhythmia with slow and persistent ventricular response, during a detection period of 24 hours, when (1) the number of the identified slow rate windows exceeds a first threshold of 400; and (2) the number of slow rate windows in the identified longest consecutive sequence exceeds a second threshold of 100.

8. The system of claim 5, wherein the one or more SSW sequences are each represented by a consecutive sequence of slow rate windows, and
wherein the heart rate analyzer circuit is configured to identify a subset of the SSW sequences each exceeding an SSW duration threshold, and to determine the second prevalence indicator based on an accumulated number of slow rate windows of the identified subset of SSW sequences.

9. The system of claim 5, wherein the one or more SSW sequences are each represented by a sequence of heart rate analysis window that includes, for any ten consecutive heat rate analysis windows within the sequence, at least six slow rate windows, and
wherein the heart rate analyzer circuit is configured to identify a longest SSW sequence among the identified SSW sequences, and to determine the second prevalence indicator indicating a number of heart rate analysis windows included in the identified longest SSW sequence.

10. The system of claim 1, wherein the SSB sequences are each represented by a consecutive sequence of two or more of the identified slow heart beats.

11. The system of claim 1, wherein the SSB sequences are each represented by a beat sequence that includes, for any ten consecutive heart beats within the beat sequence, at least six slow heart beats.

12. The system of claim 1, wherein the arrhythmia detector circuit is configured to detect the slow and persistent rhythm including an atrial arrhythmia with slow and persistent ventricular response.

13. A method for detecting cardiac arrhythmias using a medical system, the method comprising:
monitoring a ventricular heart rate corresponding to a plurality of heart beats using a heart rate analyzer circuit;
identifying, from the plurality of heart beats during a detection period, slow heart beats with corresponding heart rates falling below a rate threshold using the heart rate analyzer circuit;
identifying, during the detection period, one or more sustained slow beat (SSB) sequences each including two or more of the slow heart beats using the heart rate analyzer circuit; and
detecting a slow and persistent rhythm based on the identified slow heart beats and the identified one or more SSB sequences using an arrhythmia detector circuit.

14. The method of claim 13, comprising determining a first prevalence indicator of the identified slow heart beats, and a second prevalence indicator of the one or more SSB sequences using heart rate analyzer circuit, wherein detecting the slow and persistent rhythm includes determining that the first determined prevalence indicator exceeds a first prevalence threshold and the second determined prevalence indicator exceeds a second prevalence threshold.

15. The method of claim 14, wherein the first prevalence indicator includes an accumulated duration of the identified slow heart beats, and the second prevalence indicator includes a duration of a longest SSB sequence among the identified one or more SSB sequences.

16. The method of claim 14, wherein the second prevalence indicator includes an accumulated duration of a subset of the identified one or more SSB sequences each exceeding an SSB duration threshold.

17. The method of claim 14, comprising:
determining a representative ventricular heart rate for each of a plurality of heart rate analysis windows, the plurality of heart rate analysis windows each including two or more of the plurality of heart beats;
identifying, from the plurality of heart rate analysis windows during the detection period, slow rate windows with corresponding representative ventricular heart rates falling below the rate threshold;
identifying, during the detection period, one or more sustained slow window (SSW) sequences each including two or more of the identified slow rate windows; and
determining the first prevalence indicator indicating a number of the identified slow rate windows, and a second prevalence indicator of the identified one or more SSW sequences.

18. The method of claim 13, wherein the SSB sequences are each represented by a consecutive sequence of two or more of the identified slow heart beats.

19. The method of claim 13, wherein the SSB sequences are each represented by a beat sequence that includes, for any ten consecutive heart beats within the beat sequence, at least six slow heart beats.

20. The method of claim 13, comprising delivering a therapy to a target tissue in response to the detection of the slow and persistent rhythm.

* * * * *